United States Patent [19]

Quadro et al.

[11] Patent Number: 4,956,389
[45] Date of Patent: Sep. 11, 1990

[54] COMPOUNDS HAVING CALCIUM BLOCKING ACTIVITY

[75] Inventors: Giuseppe Quadro, Milan, Italy; Jean Cahn, Montrouge, France

[73] Assignees: Yason S.R.L., Milan, Italy; SIR International S.A., Montrouge, France

[21] Appl. No.: 691,157

[22] Filed: Jan. 14, 1985

Related U.S. Application Data

[63] Continuation of Ser. No. 512,170, Jul. 8, 1983, abandoned.

[30] Foreign Application Priority Data

Jul. 9, 1982 [IT] Italy ............................... 22339 A/82
Apr. 28, 1983 [IT] Italy ............................... 20838 A/82

[51] Int. Cl.$^5$ ..................... A61K 31/135; C07C 87/28
[52] U.S. Cl. .................................... 514/654; 514/821; 564/374
[58] Field of Search ..................... 564/374; 514/654

[56] References Cited

U.S. PATENT DOCUMENTS 4,181,738  1/1980  Gines et al. .......................... 510/654

Primary Examiner—Robert V. Hines
Attorney, Agent, or Firm—Bucknam and Archer

[57] ABSTRACT

Compound of general formula I

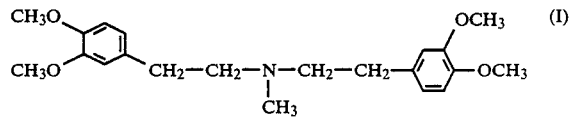

and its addition salts with a pharmaceutically acceptable acid is described. The compound is prepared by reacting bis-(2-(3,4-dimethoxy-phenyl)ethyl)amine with formaldehyde in a reducing medium. The compound is effective in the treatment of cardiovascular diseases and disturbances in cerebral circulation.

1 Claim, No Drawings

COMPOUNDS HAVING CALCIUM BLOCKING ACTIVITY

This is a continuation of application Ser. No. 512,170, filed July 8, 1983 and now abandoned.

DESCRIPTION OF THE INVENTION

The present invention relates to N-methyl-N-bis-(3,4-dimethoxy-phenyl-ethyl)amine of general formula I

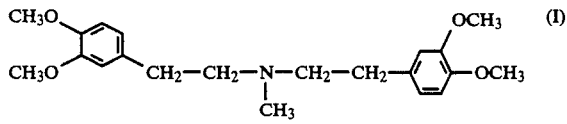

having calcium antagonistic activity.

The compound according to the invention, which has a very low toxicity, is therefore useful in the therapy of cardiovascular diseases and irregularities in the cerebral circulation.

Rosenmund, Külz, and Buth, in U.S. Pat. No. 2,006,114, in Ber. 72 B 18–28, 1939 and in DE No. 617647 have reported the synthesis of a series of bis-phenethylethyl amines endowed with papaverine-like and spasmolytic properties, describing also N-methyl-N-bis-(3,4-dimethoxy-phenyl-ethyl)amine.

As a matter of fact, the compound cited by Rosenmund et al. (for which said authors do not give any data supporting its structure) must have a structure different from that of the compound claimed in this invention, because for its hydrochloride the authors report a m.p. of 230° or 242° C., whereas the hydrochloride of the compound here obtained (whose structure, on the contrary, is demonstrated by the NMR data), melts at 180°–185° C. even after repeated crystallizations and in a state of high purity. Moreover, as it will be pointed out hereinafter, it has been noticed a marked difference even in the pharmacological properties of the compound according to this invention and the compound mentioned by Rosenmund et al. Probably, the different nature of the latter compound must be related to the fact that the corresponding not N-methylated secondary amine is obtained according to a quite unusual reaction, i.e. the hydrogenolysis of (3,4-dimethoxy-phenethyl)-amine with $H_2$ on $Pd/BaSO_4$ at very high temperatures, according to the following scheme:

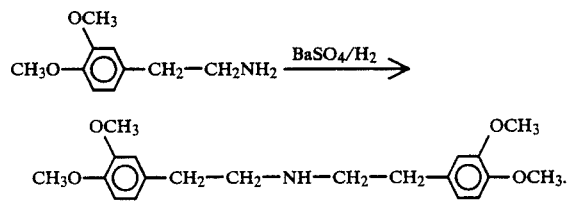

Moreover the German Patent No. 617647 describes the methylation of said secondary amine with formaldehyde, in absence of any reducing agent; in U.S. Pat. No. 2,006,114 the methylation is carried out in the presence of formic acid, but nevertheless the corresponding hydrochloride has an even higher melting point (242°) in comparison with the hydrochloride of N-methyl-N-bis-(3,4-dimethoxy-phenyl-ethyl)-amine, whose structure as it was stressed above, has been herein rigorously confirmed. On the contrary, according to the teachings of the above cited references a different compound is obtained as it has been found by repeating the same experimental methods described therein.

As a consequence, compound (I) must be considered new.

The pharmacological properties of compound (I) weren't also foreseeable from its structure related to papaverine.

It is known in fact, that the therapeutic actions of papaverine have been doubted, see for instance Goodman and Gilman's "Pharmacological Basis of Therapeutics" McMillan, New York, 830 Needleman and Johnson, where it is stated that "papaverine has not been demonstrated to be of therapeutic value in any condition".

Similar conclusions were also drafted by an experts' committee of U.S. Food and Drug Administration, who stated that there aren't elements to prove the papaverine's efficacy in any of the indications cited by the manufacturers.

On the ground of these conclusions, the FDA proposed to withdraw papaverin from the market (FDA Drug Bull. 9, 26, 1979; Fed. Reg. 44, 30443, 1979).

The compounds described in the above mentioned patents and reference were therefore never used in therapy and no therapeutical indications could be derived by the teachings of the prior art.

We have now surprisingly found that the compound of formula I, exhibits a strong calcium antagonistic activity, comparable to nifedipine (a known and recent calcium antagonistic drug) and not related to papaverine-like properties.

In fact, the actions of papaverine on the calcium ion are complex and characterized by a stimulation of calcium ion flows at the lower concentrations (Carpenedo et al. J. Pharm. Pharmacol. 1971, 23, 502–505) and by and antagonism at concentrations of about $10^{-4}M$ (Sanguinetti and West, J. Pharm. Exp. Ther., 219, 715, 1981).

The same authors also showed that papaverine and verapamil, a known calcium-antagonist, are mutually antagonistic on the slow entry flows sustained by calcium ions in isolated guinea-pig atria.

Papaverine is therefore totally devoid of calcium antagonistic activity and the same characteristic should be expected for structurally related compounds.

Moreover, the main biochemical action of papaverin and some of its derivatives is the inhibition of phosphodiesterases (Kukovetz and Pöch, Naunyn Schmiedebergs Arch. Pharm., 267, 189–194, 1970). On the contrary, we have surprisingly found that N-methyl-N-bis-(3,4-dimethoxy-phenyl-ethyl)-amine, besides having a strong calcium antagonistic activity, is completely devoid of inhibiting activity on the phosphodiesterases.

The therapeutic and pharmacological profile of the compounds of the invention must be therefore considered unforeseeable, on the ground both of the above cited references and of the pharmacology of papaverine, in spite of possible structural analogies.

The compounds of the invention are therefore new therapeutical agents blocking the calcium entry, useful in the myocardial ischemia and in cerebro-vascular diseases caused by cerebral oligoemia.

The compound according to the invention is prepared from bis-(2-(3,4-dimethoxyphenyl)ethyl)amine under conditions of reducing amination, that is by treatment with formaldehyde in a reducing medium.

The following example is submitted by way of illustration of the invention.

EXAMPLE

(a) 3,4-Dimethoxyphenylacetyl chloride 29.5 g of 3,4-dimethoxyphenyl-acetic acid are dissolved in 200 cc of anhydrous chloroform free from ethanol. There is then added 23.8 g of thionyl chloride. The mixture is warmed under reflux for four hours. The solvent and the excess of reagent are then removed under reduced pressure. The oily residue is distilled under reduced pressure (10 mmHg) collecting the fraction which distills at 170°-172° C. The pure acid chloride is thus obtained; 26 g, yield 81%.

(b) N-(2-(3,4-Dimethoxyphenyl)ethyl)-3,4-dimethoxyphenylacetamide 21.7 g of 2-(3,4-dimethoxyphenyl)ethylamine are dissolved in 150 cc of anhydrous chloroform and then the solution is added to 15.2 g of anhydrous triethylamine. The solution is cooled at a temperature between 5° and 10° C. and then, under stirring, there is added the 3,4-dimethoxyphenylacetyl chloride prepared in part (a), 26 g, dissolved in 80 cc of anhydrous chloroform. The temperature is allowed to rise to room temperature. It is then warmed under reflux for eight hours. After cooling the mixture, by addition of an additional portion of chloroform, 200 cc, the organic phase is washed with water and then with 5% hydrochloric acid and an additional amount of water, then 5% sodium hydroxide and finally water. The organic phase is dried over anhydrous sodium sulfate and after filtering, the solvent is evaporated under reduced pressure. The solid thus obtained is recrystallized from absolute ethanol. The pure amide, 36 g, is obtained in a yield of 84%, m.p. 128° C. The substance gives a single spot on chromatography using ethanol as eluent.

(c) Bis-(2-(3,4-dimethoxyphenyl)ethyl)amine 37.7 g of sodium borohydride are suspended in 1500 cc of anhydrous tetrahydrofuran in an inert atmosphere of nitrogen. To the suspension are added 36 g of amide prepared in part (b), while the mixture is stirred and cooled to 10° C., and there is added also 58 cc of glacial acetic acid. The mixture is warmed under reflux for four hours. At the end of this period, the solvent is evaporated under reduced pressure and the residue is treated with water and then with dilute hydrochloric acid to a full acidity. To the mixture is then added a solution of sodium hydroxide until the pH is alkaline and the material is extracted four times with 300 cc each time of dichloromethane. The organic phase is extracted with dilute hydrochloric acid, the acetic solution is washed with dichloromethane. It is then cooled and made alkaline with potassium carbonate and finally extracted again with four portions of dichloromethane, using 200 cc each time. The organic phase is dried over anhydrous sodium sulfate, filtered and evaporated. The residue is the crude amine which is recrystallized from ethanol thus giving a pure product, 28.5 g, yield 75%; m.p. 56°-58° C. A single spot is obtained on T.L.C. (eluent: n-butanol, ethanol, acetic acid, water 60:20:40:10).

Elementary Analysis: Calcd. % C=69.54; H=7.88; N=4.05; Found % C=69.77; H=8.01; N=4.16.

(d) N-methyl-N-bis-(3,4-dimethoxy-phenyl-ethyl)amine

The compound prepared in part (c), 10.4 g, is dissolved in 100 cc of methanol and 30 cc of 37% of formaldehyde are added. The mixture is boiled under stirring for 40 minutes, it is then cooled with an ice bath to 0° C. and 4 g of $NaBH_4$ are added in small portions. Stirring is continued at room temperature for 1½ hours and then methanol is evaporated under reduced pressure. The residue is dissolved in water, acidified with hydrochloric acid. After having stirred for a few minutes, it is cooled and it is then made definitely alkaline with sodium hydroxide solution. The alkaline solution is extracted with dichloromethane, the organic phase is isolated, washed with water, dried over $Na_2SO_4$. It is then filtered and the solvent evaporated under reduce pressure to dryness.

The residue is crystallized twice from n-hexane, using 100 cc each time, thus obtaining a pure product, 6.7 g, 62% yield; m.p. 67°-69° C. The product gives a single chromatographic spot in T.L.C. using the same eluent as in the case of the amine under (c).

Elementary Analysis for $C_{21}H_{29}NO_4$ (mol.wt.=359.47); Calcd. % C=70.16; H=8.13; N=3.89; Found % C=70.23; H=8.17; N=3.85.

The compound thus obtained is designated hereinbelow with the symbol YS 035. The structure of the compound has been confirmed by spectroscopic data.

Spectrum $H^1$ NMR (registered in $CDCl_3$, using TMS as internal reference). The values of the chemical displacements of the protons are expressed in δ: 2.35 (s, 3H, N-$CH_3$); 2.7 (s, 8H, N-$(CH_2-CH_2)_2$); 3.8 (s, 12H, 4 ($OCH_3$)); 6.7 (s, 6H aromatics).

The hydrochloride of the compound YS 035 exhibits a m.p. of 180°-185° C.

Elementary Analysis for $C_{21}H_{30}NO_4Cl$ (mol.wt. 395.93); Calcd. % C=63.70; H=7.63; N=3.54; Found % C=63.42; H=7.45; N=3.39.

The compound YS 035 has been subjected to a series of pharmaco-toxicological tests for the purpose of determining the activity in comparison with the known drugs Nifedipine and Nicardipine which exhibit a calcium antagonistic activity. The results so obtained are reported hereinbelow.

Acute Toxicity of YS 035

The acute toxicity has been determined by the oral route, by the venous route in male rats according to the method of Litchfield and Wilcoxon (J. Pharm. Exp. Therap., (1949), 96, p. 99). The substance YS 035 has exhibited a toxicity $DL_{50}$ of 177.9 mg/kg by the oral route and 19 mg/kg by the venous route.

PHARMACOLOGY

Calcium antagonistic activity

Inhibition of the $Ca^{2+}$-uptake in synaptosomes of the brain of rats

The synaptosomes have been prepared from an homogenate of the brain of rats by centrifugation in the gradient of Filcoll at 23,500 rpm for a period of 30 minutes and diluted to 1.5 mg/cc in the medium constituted by:

| | |
|---|---|
| NaCl | 120 mM |
| KCl | 30 mM |
| $MgSO_4$ | 1.2 mM |
| $KH_2PO_4$ | 0.4 mM |

| -continued | |
|---|---|
| NaHCO$_3$ | 5 mM |
| TES | 20 mM |
| Glucose | 10 mM |

The substance YS 035 and nifedipine and papaverine, by way of comparison, have been added to the medium at a final concentration of 250 μM. After 15 minutes of preincubation, $^{45}$CaCl$_2$, final concentration 1 mM (0.2μCi/cc is added to the medium).

The first determination has been carried out two minutes after the addition. The concentrations which have been found have been set as values at 0 time. The other controls have been carried out after 5 minutes, 10 minutes and 15 minutes. After each period, the reaction has been stopped by centrifugation and the radioactivity has been determined in the supernatant as well as in the pellet. The latter had been denatured previously with PCA, neutralized and subsequently centrifuged.

The results illustrated in the following Table 1 are expressed as the quantity of calcium transferred per mg of protein after the maximum period of incubation of 15 minutes.

TABLE 1

| Compound | Ca$^{2+}$- uptake (n g ions/mg prot/15 min) |
|---|---|
| Control | 80 ± 7 |
| Papaverine (250 μM) | 79 ± 5 |
| Nifedipine (250 μM) | 42 ± 5 |
| YS 035 (250 μM) | 47 ± 4 |

On the basis of the data in the table, it is possible to note that the inhibitory activity on the calcium uptake exhibited by the new substance YS 035 in the synaptosomes of the brain of rats is comparable to the activity exhibited by Nifedipine, while papaverine is completely devoid of calcium antagonistic activity.

Inhibition of Ca$^{2+}$-uptake in kidney cells in newborn hamsters

Cells of kidneys of newborn hamsters have been washed and then resuspended several times in concentration of 5·10$^6$/cc in the medium of the following composition:

| NaCl | 120 mM |
|---|---|
| KCl | 5.5 mM |
| Glucose | 5.5 mM |
| Na$_2$HPO$_4$ | 0.7 mM |
| NaHCO$_3$ | 25 mM |
| MgCl$_2$ | 1.3 mM |
| TRIS.HCl at pH 7.4 | 10 mM |

The substance YS 035 and nifedipine by comparison were added at a final concentration of 250 μM.

After 15 minutes of preincubation at 30° C., the reaction was made to begin by addition to the medium of $^{45}$CaCl$_2$ 1 mM (0.1μCi/cc). The concentrations at 0 period of time were the concentrations determined two minutes after the addition. The other controls were carried out after 5 minutes, 10 minutes, and 20 minutes. The determination of [Ca$^{2+}$] was carried out as in the preceding experiment.

The results are reported in Table 2 as the quantity of Ca transferred per mg of protein, (1 mg of protein=5·10$^6$ cells) at the maximum period of incubation of 15 minutes. The results obtained demonstrate in this experimental model the inhibitory action on the uptake of Ca which is exhibited both by the compound YS 035 as well as nifedipine. The activity of the new compound, however, in quantitative terms is superior to the activity of nifedipine.

TABLE 2

| Composition | Ca$^{2+}$-uptake (n g ions/mg prot/15') |
|---|---|
| — | 11.9 |
| YS 035 | 7.5 (−36.9% of inhibition) |
| nifedipine | 7.9 (−33.6% of inhibition) |

Inhibition of Ca$^{2+}$-uptake in mitochondria of liver of rats

The mitochondria prepared according to classical methods are diluted to a concentration of 1.5 mg/cc in a medium of incubation which has the following composition:

| Saccharose | 200 mM |
|---|---|
| KCl | 20 mM |
| TRIS.HCl at pH 7.4 | 10 mM |
| Succinate | 2 mM |
| Rotenone | 1 μM. |

The compound YS 035 and nifedipine by comparison were added to the medium to a final concentration of 250 μM. After a period of 15 minutes of preincubation at 20° C. there was added $^{45}$CaCl$_2$ (50 n mol/mg prot.).

In a manner analogous to the preceding experiments, the concentrations determined after two minutes were called the concentration at 0 period of time. The other controls were determined after 5 minutes, after 10 minutes and after 15 minutes. For the determination of Ca$^{2+}$, the experiment was carried out in a manner analogous to the preceding experiments.

The results are reported in Table 3 as the quantity of Ca transferred per mg of protein

TABLE 3

| Composition | Ca$^{2+}$-uptake (n g ions/mg prot.) |
|---|---|
| — | 14.3 |
| Nifedipine | 9.5 |
| YS 035 | 11.0 |

The inhibitory activity of the compound YS 035 on the uptake of Ca on the mitochondria of liver of rats is clear from these results, although under these experimental conditions, it is slightly inferior to the activity of nifedipine.

Study on the Ca$^{2+}$-efflux in mitochondria of liver of rats

The mitochondria of liver of rats prepared as in the preceding experiment were "charged" with Ca and subsequently, taken in a medium deprived of this ion. In the presence of an uncoupling agent or "Ruthenium Red", there is a flow of Ca$^{2+}$ ion from the mitochondria into the medium.

The substances YS 035 and nifedipine were added in a concentration of 250 μM both in the presence as well as in the absence of the two types of activators for the inflow of Ca.

The results reported in Table 4 are expressed as the quantity of Ca transferred from the mitochondria per mg of protein per minute. On the basis of these data, an uncoupling action of nifedipine has been noted but the substance YS 035 does not exhibit this action.

TABLE 4

| Composition | $Ca^{2+}$-efflux (n g ions/min. mg/prot) induced by: | | |
|---|---|---|---|
| | | Ruthenium red | uncoupling agent |
| — | 0.0 | 0.7 | 8.3 |
| Nifedipine (250 μM) | 3.8 | 2.2 | 8.5 |
| YS 035 (250 μM) | 0.0 | 0.6 | 5.4 |

Antagonistic activity on the contractions produced by arachidonic acid on the aorta of rabbits Study in vitro The study has been carried out by comparison with Nicardipine using autologous blood as the perfusion liquid. The addition of 0.1 mg of arachidonate to the liquid induces an isometric contraction of the aorta which is registered by a transducer. From the results reported in Table 5, the inhibitory effect of the two products on the contraction produced by the arachidonate is comparable because both molecules may induce a "by-pass" between the synthesis of Thromboxane $A_2$ and the synthesis of $PGI_2$. This phenomenon is shown by the relaxation which follows the addition of arachidonate to the perfusion blood. This effect may be noted with 0.1 mg/kg of YS 035 and 1 mg/kg of Nicardipine.

TABLE 5

| Compound | Contraction of the first portion of the aorta (mm) N = 4 | Contraction of the second and third portion of the aorta | | |
|---|---|---|---|---|
| | | dose mg · Kg$^{-1}$ | N | % Variation |
| YS 035 | 48 ± 6.7 | 0.01 | 3 | −42 ± 31.0 |
| | | 0.1 | 4 | (−60 ± 29.3) |
| | | 1.0 | 1 | −132 ± 16.1) −16 |
| Nicardipine | 38 ± 4.9 | 0.01 | 1 | −6 |
| | | 0.1 | 4 | −48 ± 15.5 |
| | | 1.0 | 3 | (−84) − 162 |

N = Total number of the portions of the aorta being examined values of the small contractions observed occasionally prior to relaxation.

Inhibition of the phosphodiesterase activity

The inhibition of phosphodiesterase activity of YS 035 and of papaverine has been assessed according to the method of K. G. Nair (Biochemistry, 5, 150, 1966). It has been used a medium containing:
2.5 ml of buffer tris-HCl 0.1M pH 7.4;
50 μl MgSO$_4$.7H$_2$O (10 μg/ml);
50 μl CAMP "Sigma" (1 mg/ml);
5 μl Adenosin deaminase (2 mg/ml);
20 μl of alkaline phosphatase "Sigma" (2.6 mg/ml);
15 μl of phosphodiesterase (10 mg/ml).

YS 035 has been added up to a final concentration of 100 mM and Papaverine to a concentration of 10 mM. The ID$_{50}$ values (inhibiting dose 50%) proved to be 0.04 mM for papaverine, while YS 035 proved to be completely inactive.

Studies in vivo

Both substances YS 035 and Nicardipine have been administered orally for a period of three consecutive days to rabbits in such a manner that the last administration of each substance was carried out one hour prior to killing the animals. The portions of the aorta had then been incubated either in PRP as well as in the Krebs-Henseleit liquid.

The results obtained following the addition of arachidonic acid are reported in Table 6 hereinbelow:

TABLE 6

| Compound | Dose mg · Kg$^{-1}$ P.O | Amplitude of contraction (mm) | | | |
|---|---|---|---|---|---|
| | | PRP | | | Krebs |
| | | Individual Values | M ± ES | medium Individ. Values | m ± ES |
| Controls | — | +26 | 30 ± 8.0 | +4 | 12 ± 2.3 |
| | | +48 | | +25 | |
| | | +23 | | +12 | |
| | | +20 | | +10 | |
| | | +35 | | +8 | |
| | | +37 | | +8 | |
| | | +36 | | +18 | |
| | | +16 | | +12 | |
| Nicardipine | 1 | +24 | — | −30 | — |
| | | +55 | | −10 | |
| YS 035 | 10 | +28 | — | −6 | — |
| | | +28 | | +7 | |

This study demonstrates that both YS 035, as well as Nicardipine, act directly on the synthesis of prostaglandin and particularly PGI$_2$ at the aortic endothelial level rather than acting on the vasoconstrictive effect of Thromboxane A$_2$ on the platelets.

Effect on the Multiple cerebral infarct in rats

The intracarotid injection of sodium arachidonate (0.1 mg) causes in rats an edema reaction accompanied by an accumulation of calcium in the brain tissue and a decrease, on the other hand, of the cholesterol level. The substance YS 035 administered intravenously 15 minutes prior to the infarct in the dose of 1, 3.3 and 10 mg/kg reduces moderately the entry of calcium at 1 mg/kg level but exhibits no effect on the other changes at the biochemical level.

Antagonistic effect to biochemical disturbances and neurological deficiency during the post-oligemic period in rats Oligemia in rats is caused by simultaneous bilateral occlusion of the carotid arteries associated with a slight decrease (8–9 kPa) of blood pressure and is maintained for 60 minutes. After removal of the occlusion, the post-oligemic period is followed for several days. In this case, the observation is continued up to the third day, at the time during which the brain accumulation of Ca++ ions reaches the maximum.

The substances YS 035 or Nicardipine respectively, are administered to rats, 1, 5, 18, 24, 42 and 71 hours after having removed the carotid occlusion. The rats are sacrificed after 72 hours and the tissues are rapidly removed in order to determine their content of water, calcium and potassium. The results are summarized in the following Table 7:

TABLE 7

| Group | N 7× | mg · Kg$^{-1}$ P.O. | Cerebral concentration | | |
|---|---|---|---|---|---|
| | | | H$_2$O % | K+ mmol · Kg$^{-1}$ of dry substance | Ca++ |
| Controls | 36 | — | 78.7 ± 0.05 | 499.3 ± 3.45 | 4.4 ± 0.20 |
| Post-Oligemic | 11 | — | 80.1 ± 0.37 | 366.2 ± 12.58 | 28.2 ± 3.22 |
| Controls | | | *0.005 | *0.0001 | *0.0001 |

TABLE 7-continued

| | | | Cerebral concentration | | |
|---|---|---|---|---|---|
| Group | mg·Kg$^{-1}$ P.O. N | 7× | H$_2$O % | K+ mmol·Kg$^{-1}$ of dry substance | Ca++ |
| (+72 h) | | | | | |
| Nicardipine | 4 | 3 | 79.2 ± 0.42 *NS **NS | 368.5 ± 19.69 *0.01 **NS | 19.3 ± 4.92 *NS **NS |
| YS 035 | 8 | 3 | 79.0 ± 0.44 *NS **0.0309 | 420.0 ± 11.85 *0.0000 **0.004 | 10.7 ± 2.46 *0.0500 **0.0004 |

N = number of rats for each group
P = 0.05 according to the test of Student of Cochran
*against the controls
**against the post-oligemic controls The results hereinabove show that YS 035 is capable of reducing the seriousness of the cerebral edema and particularly to reduce substantially the intracellular accumulation of Ca++ ions. Also Nicardipine appears to act in the same manner, although its action is much less significant particularly with respect to the accumulation to Ca ions.

Anti-arrythmic effect and antiischemic effect in rats

The left coronary artery, when it is tied, induces in the anesthetized rats a precocious arrythmia (30 minutes) particularly ectopic beats, ventricular tachycardia (VT), ventricular fibrillation (VF) according to the methods of Selye 1960, Clark 1980 and Parratt 1982.

By injection of YS 035 intravenously, 15 minutes prior to tying up the coronary artery in the dose between 0.156 mg/kg and 20 mg/kg, the results obtained are reported hereinbelow:

TABLE 8

| | | | Significant values for each group | | | | | | |
|---|---|---|---|---|---|---|---|---|---|
| Group | Dose mg/Kg I.V. | N | No. ectopic beats | VT sec. | VF sec. | No. of phases VF (%) | Latent time | % Death | Latent Time Death (min) |
| Controls | — | 12 | 1324 | 113 | 71 | 75 | 14 | 58 | 20 |
| YS 035 | 0.156 | 5 | 907 | 34 | 4 | 40 | 22 | 20 | 26 |
| | 0.625 | 5 | 646 | 9 | 0 | 0 | 30 | 0 | >30 |
| | 1.25 | 5 | 684 | 29 | 0 | 0 | 30 | 0 | >30 |
| | 2.5 | 5 | 725 | 34 | 9 | 20 | 26 | 0 | >30 |
| | 5 | 2 | 1287 | 62 | 5 | 50 | 21 | 0 | >30 |
| | 10 | 3 | 474 | 9 | 0 | 0 | 30 | 0 | >30 |
| | 20 | 2 | 777 | 22 | 10 | 50 | 20 | 0 | >30 |

As it appears from the table, the administration by the endovenous route of the substances YS 035 prevents the onset of the most serious arrythmia such as VF and VT and the death in the dose between 0.625 and 10 mg/kg. There is no relationship between the dose and the observed effect because above a certain dose of 10 mg/kg, there is a regression of the results.

Effect on the myocardial infarct in the subacute phase in dogs

The tying up of the intraventricular coronary artery by the method of Harris causes the following effects:
(a) A decrease in the coronary blood flow
(b) An increase in the coronary vascular resistance
(c) A decrease of the index of work of the left ventricle
(d) An increase in the ratio DPTI/TTI
(e) A decrease in the index of aortic flow
(f) A decrease in the consumption of glucose, oxygen and lactate on the part of the miocardium
(g) A decrease in the uptake of free fatty acids by the myocardium.

The treatment with YS 035 in the dose of 0.1 mg/kg intravenously, carried after tying the coronary artery and three times within 48 hours in the same dose has provided the following results:
(a) The coronary blood flow remains similar to that of the control groups, or at the most tends to increase moderately during the experiment.
(b) The coronary vascular resistance not only is reduced, but becomes inferior to that of the control group.
(c) The index of work of the left ventricle is significantly higher than that present in the dogs with the infarct.
(d) The ratio DPTI/TTI is not changed.
(e) The index of the aortic flow is not changed.
(f) The consumption of glucose in the myocardium is not changed while the consumption of oxygen increases substantially and the consumption of lactate has a tendency to return to normality.
(g) The uptake of the free fatty acids increases and reaches also a value twice the basal flow measured in healthy control animals.

The present invention covers also all the applicable industrial aspects connected with the use of compounds of formula I in the cardiovascular therapy.

An essential aspect of the invention, therefore, resides in pharmaceutical compositions which contain, as active components, a compound according to formula I which may also be used together with conventional excipients normally used in formulations.

The compounds according to the invention may be administered by the oral or parenteral route: in the case of YS 035, the average dose daily by the oral route is between 20 and 150 mg in two or three administrations.

The treatment may be continued for prolonged period of time. In the case of an acute condition, the substance YS 035 may also be administered by slow infusion into the veins in the dose between 10 and 20 μg/kg.

By way of examples of the pharmaceutical compositions according to the present invention, there may be mentioned:
opercolated gelatin capsules containing 10 mg of YS 035;
compresses containing 20 mg of YS 035 in addition to excipients conventionally used in pharmaceutical formulations;
sterile phthials suitable for parenteral administration containing 1 mg/cc of YS 035 hydrochloride in sterile apyrogenic distilled water.

What is claimed is:

1. The method of treatment of a condition consisting of cardiovascular diseases due to myocardial ischemia, disturbances in cerebral circulation due to cerebral oligoemia and calcium ions accumulation, which consists of administering to a living subject affected by said condition an effective amount of the compound N-methyl-N-bis-(3,4-dimethoxy-phenyl-ethyl)amine of formula I

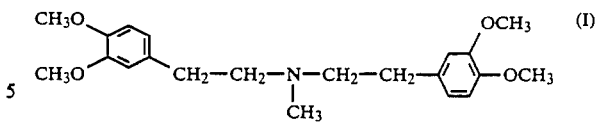

of melting point 67°-69° C. which forms a hydrochloride of melting point 182°-185° C., or an acid addition salt thereof with a pharmaceutically acceptable acid, and mixtures thereof in unit dosage form and inert excipients.

* * * * *